United States Patent [19]

Goffe et al.

[11] Patent Number: 5,684,712
[45] Date of Patent: Nov. 4, 1997

[54] APPARATUS AND METHOD FOR CELL SEPARATION

[75] Inventors: Randal A. Goffe, Bothell; George Blat, Edmonds; Michael D. Emde, Redmond; Fred Mill; Patrick M. Maloney, both of Bothell, all of Wash.

[73] Assignee: CellPro, Inc., Bothell, Wash.

[21] Appl. No.: 425,996

[22] Filed: Apr. 20, 1995

Related U.S. Application Data

[62] Division of Ser. No. 5,891, Jan. 15, 1993, abandoned, which is a division of Ser. No. 780,750, Oct. 23, 1991, Pat. No. 5,249,856.

[51] Int. Cl.$^6$ .............................. B03C 1/30; B01F 13/08
[52] U.S. Cl. .............................. 364/502; 209/8; 210/695; 366/274; 436/526
[58] Field of Search .............................. 310/80; 318/618; 364/550, 502; 366/118, 274; 388/801, 907, 907.5; 209/8; 210/695; 436/526

[56] References Cited

U.S. PATENT DOCUMENTS

| | | | |
|---|---|---|---|
| 2,459,224 | 1/1949 | Hendricks | 366/274 |
| 2,859,020 | 11/1958 | Eddy et al. | 366/274 |
| 2,958,517 | 11/1960 | Harker et al. | 259/122 |
| 3,138,370 | 6/1964 | Anderson et al. | 366/274 |
| 3,299,693 | 1/1967 | Kieselbach | 73/23.1 |
| 3,384,353 | 5/1968 | Worth | 259/108 |

(List continued on next page.)

FOREIGN PATENT DOCUMENTS

| | | |
|---|---|---|
| 288 425 A2 | 10/1988 | European Pat. Off. . |
| 323 829 | 7/1989 | European Pat. Off. . |
| 399 971 A1 | 11/1990 | European Pat. Off. . |
| 2647213 | 11/1990 | France . |
| 2010515 | 9/1971 | Germany . |
| 2914170 | 10/1980 | Germany . |

(List continued on next page.)

OTHER PUBLICATIONS

Juckett and Hultquist, "Chromatography of Erythroblasts on Immobilized Transferrin," *Proceedings of the Society for Experimental Biology and Medicine* 172:79–83, 1983.

(List continued on next page.)

*Primary Examiner*—Edward R. Cosimano
*Attorney, Agent, or Firm*—Seed and Berry LLP

[57] ABSTRACT

An improved cell separator is provided that includes apparatus for automatically controlling the cell separation process. Particularly, a plurality of valves are responsive to a data processor assembly for controlling the path of fluid flow through the cell separator. A plurality of sensors are provided for providing sensor signals indicative of the density of fluid flowing through the cell separator. The microprocessor is responsive to the sensor signals for controlling the flow and operation of the cell separator. A parastaltic pump is responsive to the microprocessor assembly for controlling the speed and direction of fluid flow through the system. A stirplate assembly is responsive to a drive signal from the data processor assembly for controllably agitating the contents of a column. The data processor assembly is further responsive to the sensor input to provide the valve control signals and pump control signal to control the concentration of selected cells that are collected. The improved cell separator further includes an improved stirplate assembly having a column with a stirbar rotatably supported therein. The stirbar includes a magnet section and a stem extending outward from the magnet section. First and second propellor blades are mounted to the stem for increasing the agitation provided to the contents of the column by the stirbar. A stirplate is provided for developing a rotating magnetic field, magnetically coupled to the stirbar magnets, to rotate the stirbar. The stirplate includes a Hall effect sensor for providing a stirbar position signal indicative of the change in magnetic field as a result of rotation of the magnets. The cell separator data processor is responsive to the stirbar position signal for controlling the change in the moving magnetic field thereby to control the speed of rotation of the stirbar.

3 Claims, 6 Drawing Sheets

U.S. PATENT DOCUMENTS

| | | | |
|---|---|---|---|
| 3,433,465 | 3/1969 | Szpur | 366/274 X |
| 3,554,497 | 1/1971 | Zipperer | 366/274 X |
| 3,645,687 | 2/1972 | Nerenberg | 23/230 |
| 3,694,341 | 9/1972 | Luck, Jr. | 204/273 |
| 3,893,920 | 7/1975 | Hubbard et al. | 210/197 |
| 4,082,668 | 4/1978 | Zeineh et al. | 210/129 |
| 4,162,855 | 7/1979 | Bender | 366/274 |
| 4,199,265 | 4/1980 | Sanderson et al. | 366/274 |
| 4,209,259 | 6/1980 | Rains et al. | 366/273 |
| 4,322,298 | 3/1982 | Persidsky | 210/787 |
| 4,355,906 | 10/1982 | Ono | 366/274 |
| 4,452,773 | 6/1984 | Molday | 424/1.37 |
| 4,516,060 | 5/1985 | Guzik et al. | 318/618 X |
| 4,523,996 | 6/1985 | Charles et al. | 210/504 |
| 4,599,170 | 7/1986 | Friedman et al. | 210/223 |
| 4,653,519 | 3/1987 | Kanner | 134/140 |
| 4,675,286 | 6/1987 | Calenoff | 435/7 |
| 4,734,372 | 3/1988 | Rotman | 435/291 |
| 4,761,366 | 8/1988 | Nakajima et al. | 435/2 |
| 4,840,730 | 6/1989 | Saxena | 210/198.2 |
| 4,842,730 | 6/1989 | James et al. | 210/198.2 |
| 4,915,847 | 4/1990 | Dillon et al. | 210/737 |
| 4,985,792 | 1/1991 | Moir | 360/99.08 |
| 4,993,841 | 2/1991 | Löfgren et al. | 366/274 |
| 5,080,784 | 1/1992 | James et al. | 210/198.2 |
| 5,098,842 | 3/1992 | Nakajima et al. | 435/287 |
| 5,108,904 | 4/1992 | Landay | 435/7.24 |
| 5,180,504 | 1/1993 | Johnson et al. | 210/767 |
| 5,215,927 | 6/1993 | Berenson et al. | 436/541 |
| 5,225,353 | 7/1993 | Berenson et al. | 436/541 |
| 5,240,856 | 8/1993 | Goffe et al. | 435/299 |
| 5,262,334 | 11/1993 | Berenson et al. | 436/541 |
| 5,336,760 | 8/1994 | Hardwick et al. | 530/413 |
| 5,396,757 | 3/1995 | Kobayashi et al. | 310/80 |
| 5,411,378 | 5/1995 | Sipin | 417/360 |
| 5,533,800 | 7/1996 | Stiegelmann et al. | 366/142 |

FOREIGN PATENT DOCUMENTS

| | | |
|---|---|---|
| 62-277135 | 12/1987 | Japan . |
| 1-130722 | 5/1989 | Japan . |
| WO90/04784 | 5/1990 | WIPO . |
| WO90/11126 | 10/1990 | WIPO . |
| WO90/14586 | 11/1990 | WIPO . |

OTHER PUBLICATIONS

Wigzell and Andersson, "Cell Separation on Antigen–Coated Columns. Elimination of High Rate Antibody–Forming Cells and Immunological Memory Cells", *Journal of Experimental Medicine* 129(1):23–36, 1969.

Edelman and Rutishauser, "Specific fractionation and manipulation of cells with chemically derivatized fibers and surfaces," *Methods in Enzymology* 34: 195–225, 1974.

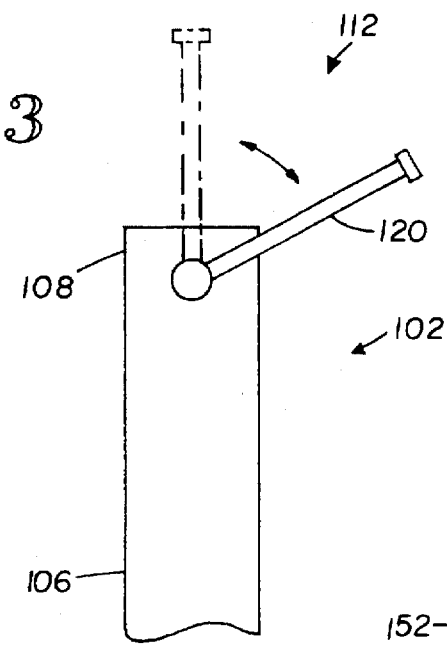
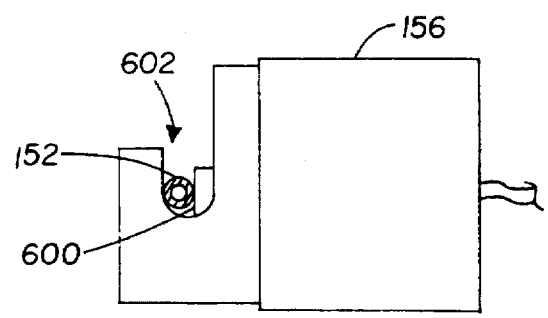
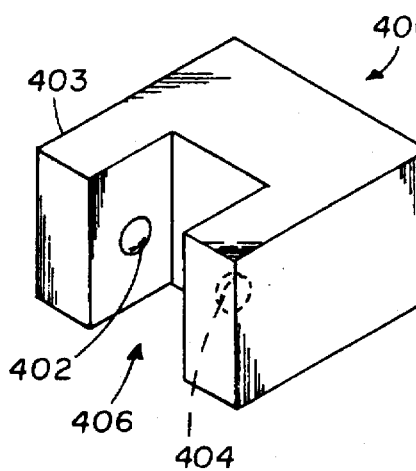
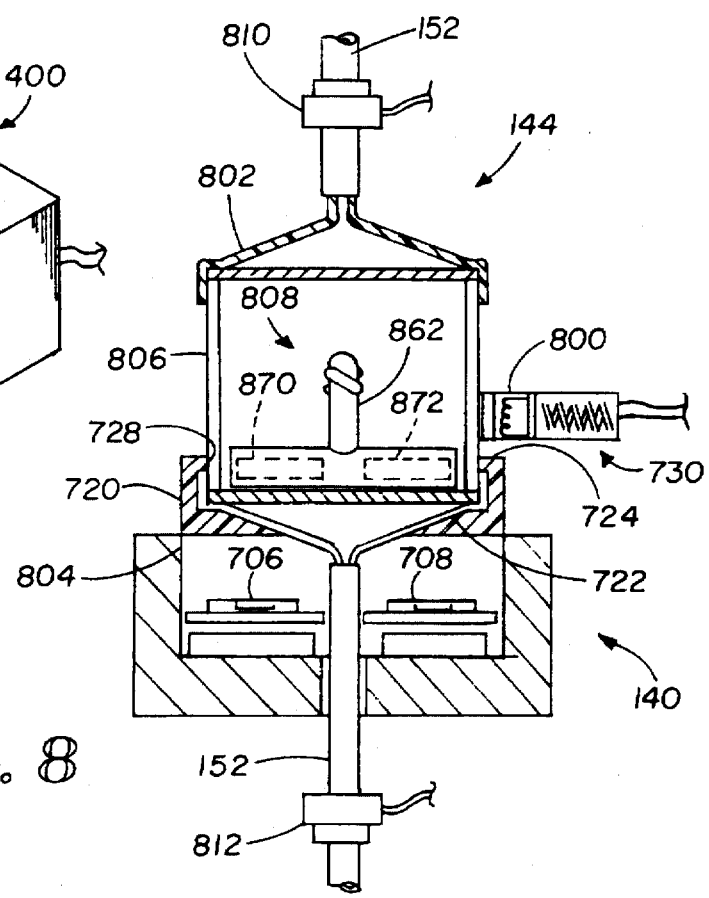

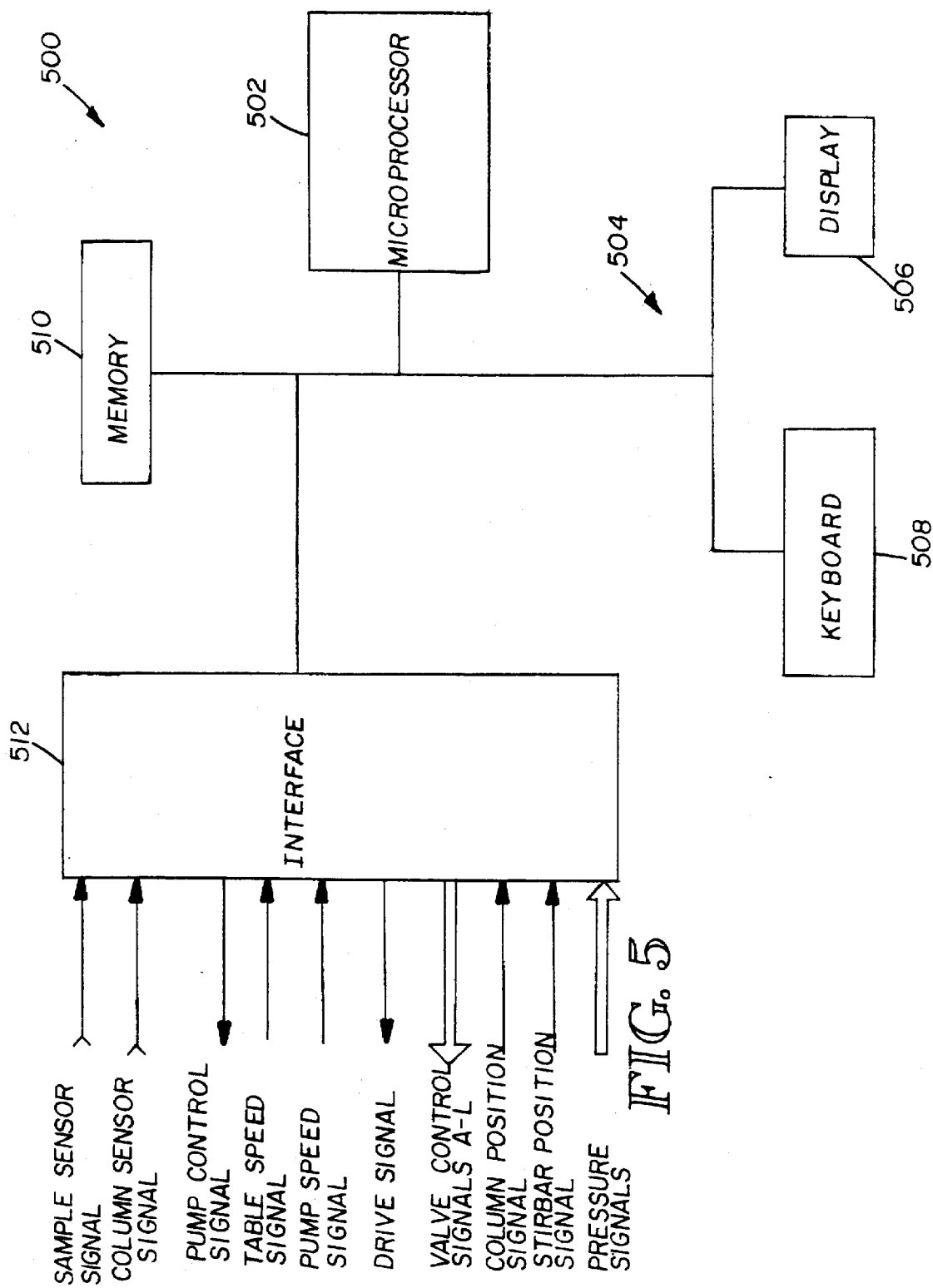

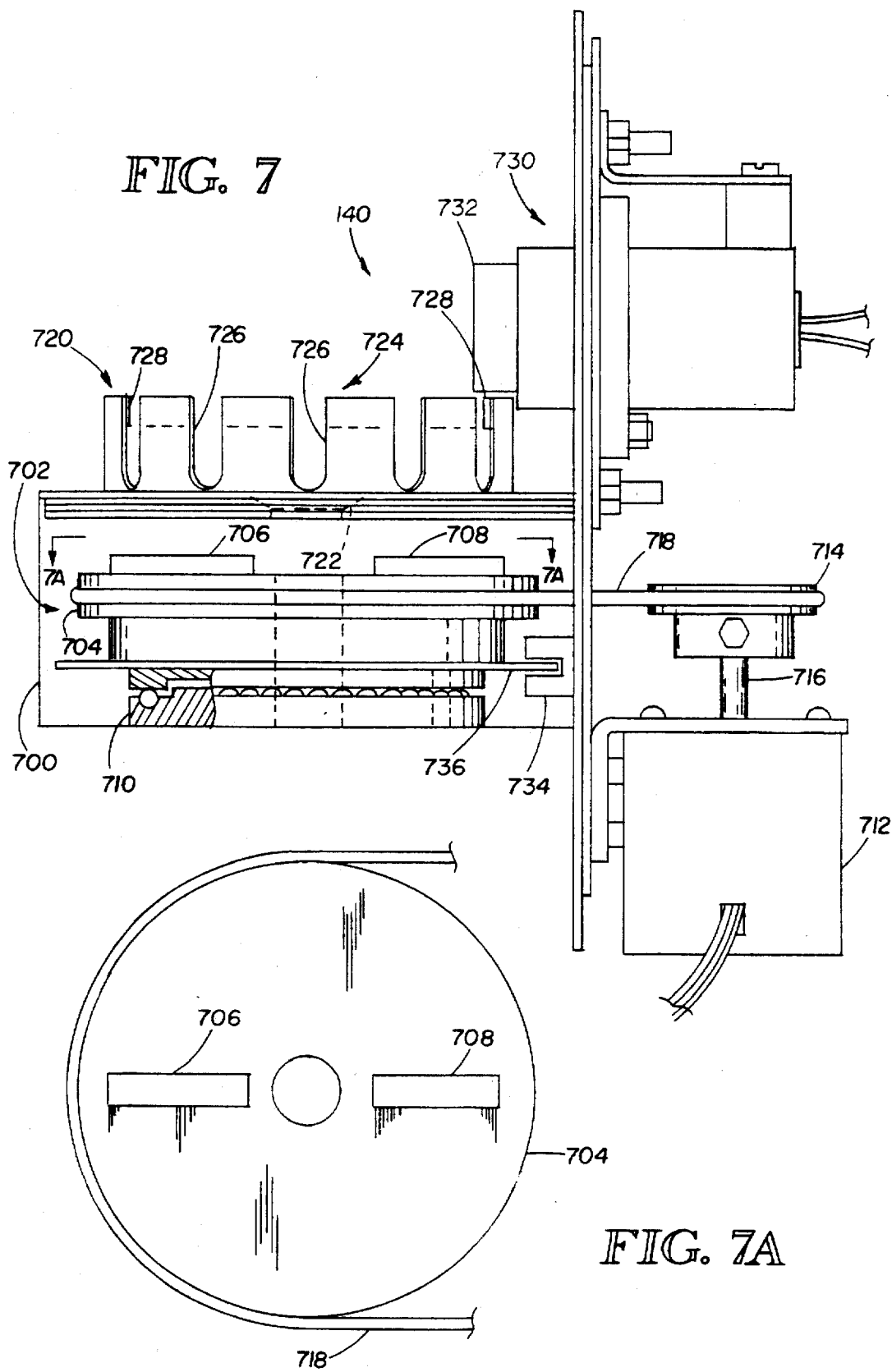

APPARATUS AND METHOD FOR CELL SEPARATION

CROSS-REFERENCE TO RELATED APPLICATIONS

This application is a division of U.S. patent application Ser. No. 08/005,891, filed Jan. 15, 1993, now abandoned; which is a division of U.S. patent application Ser. No. 07/780,750, filed Oct. 23, 1991, issued as U.S. Pat. No. 5,240,856.

TECHNICAL FIELD

The present invention is directed in general toward methods and apparatus for selecting target particles from a sample fluid and, more particularly, toward improved apparatus for controlling the operation of a device for performing immunoselection of target cells.

BACKGROUND OF THE INVENTION

Various methods and devices exist for separating component parts of a sample fluid to obtain target particles. These methods include filters, centrifuges, chromatographs, and other well-known fluid separation methods. Other apparatus and methods exist for separating a particular cell subpopulation, or target cells, from a mixture of cells. These methods include gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads. Such immunoselection methods have been used to either positively or negatively select target cells, wherein positive selection refers to the direct selection and recovery of specific target cells, while negative selection refers to the elimination of a specific target cell subpopulation from a heterogeneous population of cells.

Columns are common to the above described methods for general separation of target particles from a sample fluid and for the more specific immunoselection methods for selecting target cells from a sample fluid. Typically, a column has an entrance end, an exit end, and a substrate positioned intermediate the entrance and exit ends. In operation, the sample fluid is provided to the entrance end of the column and is moved through the column under pressure. As the fluid passes through the column, the substrate separates the target particle from the fluid composition so that the target particle exiting the column will be substantially pure. The target particle exiting the column is collected and retained as the collected product of the separation. Accordingly, the substrate is selected for a particular separation to separate the target particle from the sample fluid.

Various substrates exist for use with columns to separate the target particle from the sample fluid. Generally, the type of substrate selected for performing the separation will determine how the target particles are separated from the sample fluid. As an example, with substrates typically used in chromatography, the sample fluid is forced through the column under pressure using a solvent solution. The substrate is selected so that the target particles exhibit substantially different binding characteristics with the substrate than the remaining components of the sample fluid so that the time necessary for the target particles to pass through the substrate will be substantially different from the time necessary for the remaining components of the sample fluid to pass through the substrate. Accordingly, a substantially pure composition of the target particles will exit the column at a predetermined time for collection.

Referring again to immunoselection methods using column immunoadsorption devices, the substrate may contain beads that have been coated with a ligand, such as an antibody, immobilized on the surface of the beads. The ligands are selected to bind with the target particles, thereby immobilizing the target particles within the column. After an adequate amount of the fluid composition has been passed through the column to saturate the beads of the column substrate, the target particles can be liberated from the beads using various techniques. Preferably, the target particles are liberated from the beads by gently agitating the beads to break the bond between the target particles and the immobilized ligand. However, existing columns for performing immunoadsorption have proven undesirable since they have failed to provide commercially acceptable apparatus for agitating the substrate to aid in liberating the target particles. The prior art devices have also failed to provide apparatus for controlling the amount of agitation provided to the substrate, to prevent damage to the target particles and are further undesirable for this reason.

Other column separation devices, and particularly other column immunoadsorption devices, have also proven inefficient since these devices require considerable intervention from the operator to control the introduction of the sample fluid to the column as well as controlling the withdrawal of the target particle from the column. Typically, column separation devices must be actively monitored through various stages including stages for cleansing the column prior to introduction of the sample fluid and stages for passing the sample fluid through the column. These stages generally require significant intervention from the operator to perform each of the foregoing steps of the fluid separation process, and to perform substeps within these steps. Accordingly, the efficiency of these devices is necessarily limited by the skill and effectiveness of the operator controlling the process. It is desirable, therefore, to provide apparatus for performing fluid separation that minimizes the mount of intervention necessary from an operator of the apparatus. Additionally, it is desirable to provide apparatus for performing fluid separation wherein the movement of fluid through the apparatus may be precisely controlled by the separation apparatus without significant intervention by the operator.

SUMMARY OF THE INVENTION

The subject invention provides improved apparatus and method for separating target particles from a sample fluid. In one embodiment of the present invention, an improved fluid control system is provided for use with a cell separator having a column assembly. The column assembly includes a column for separating target cells from a sample fluid. The column assembly also includes a fluid collection bag for subsequently receiving the target cells from the column. The fluid control system includes a column sensor for providi indicative of the optical density of fluid flowing out of the column and into the fluid collection bag. The fluid control system also includes a column valve responsive to a column valve control signal for selectively enabling the fluid coming out of the column to flow into the fluid collection bag. A data processor is provided for controlling the operation of the fluid control system. The data processor is responsive to the column signal for providing the column valve control signal to optimize the concentrations of the target cells being collected.

In an alternative embodiment of the above described fluid control system, the column assembly includes a sample fluid supply bag for providing the sample fluid to the column and fluid tubing for coupling the column to the sample fluid supply bag and the fluid collection bag. The fluid control system further includes a pressure sensor coupleable to the column for determining the pressure of the fluid in the column. The pressure sensor includes a connector for coupling a pressure signal to the data processor. A pump is provided and is responsive to a pump control signal for controlling the speed and direction of fluid flow in the fluid tubing. The data processor is responsive to the pressure signal for providing the pump control signal to increase and decease the pressure of the fluid in the column.

In another embodiment of the invention, a cell separator is provided that includes a column assembly for separating target cells from a sample fluid. The column assembly includes a column, a sample fluid supply bag, and a fluid collection bag wherein the column is provided for receiving the sample fluid from the sample fluid supply bag and for separating the target cells from the sample fluid and retaining the target cells. The fluid collection bag is provided for subsequently receiving the target cells from the column. The cell separator includes an agitation assembly for agitating the contents of the column to assist in the release of target cells retained in the column. The agitation assembly is responsive to a drive signal for varying the amount of agitation of the contents of the column to vary the rate at which the target cells are released. The cell separator also includes a column sensor for providing a column signal indicative of the optical density of fluid flowing out of the column and into the fluid collection bag. Further, the cell separator includes a column valve that is responsive to a column valve control signal for selectively enabling the fluid coming out of the column to flow into the fluid collection bag. A data processor is provided for controlling the operation of the cell separator. The data processor is responsive to the column signal for providing the drive signal and the column valve control signal to prevent inadequate concentrations of the target cells from being collected.

BRIEF DESCRIPTION OF THE DRAWINGS

FIG. 3 is a side elevational view of a cell separator illustrating a pivotal bag holder;

FIG. 4 is a perspective view of an optical sensor of the cell separator.

FIG. 5 is an illustrative schematic diagram of a control circuit for the cell separator;

FIG. 6 is a schematic diagram illustrating the operation of a valve of the present invention;

FIG. 7 is a detailed illustrative diagram of the stirplate assembly of the cell separator;

FIG. 7A is a top plan view of the magnet table of the stirplate assembly;

FIG. 8 is a sectional diagram of the column for the cell separator; and

DETAILED DESCRIPTION OF THE INVENTION

Figure 1:
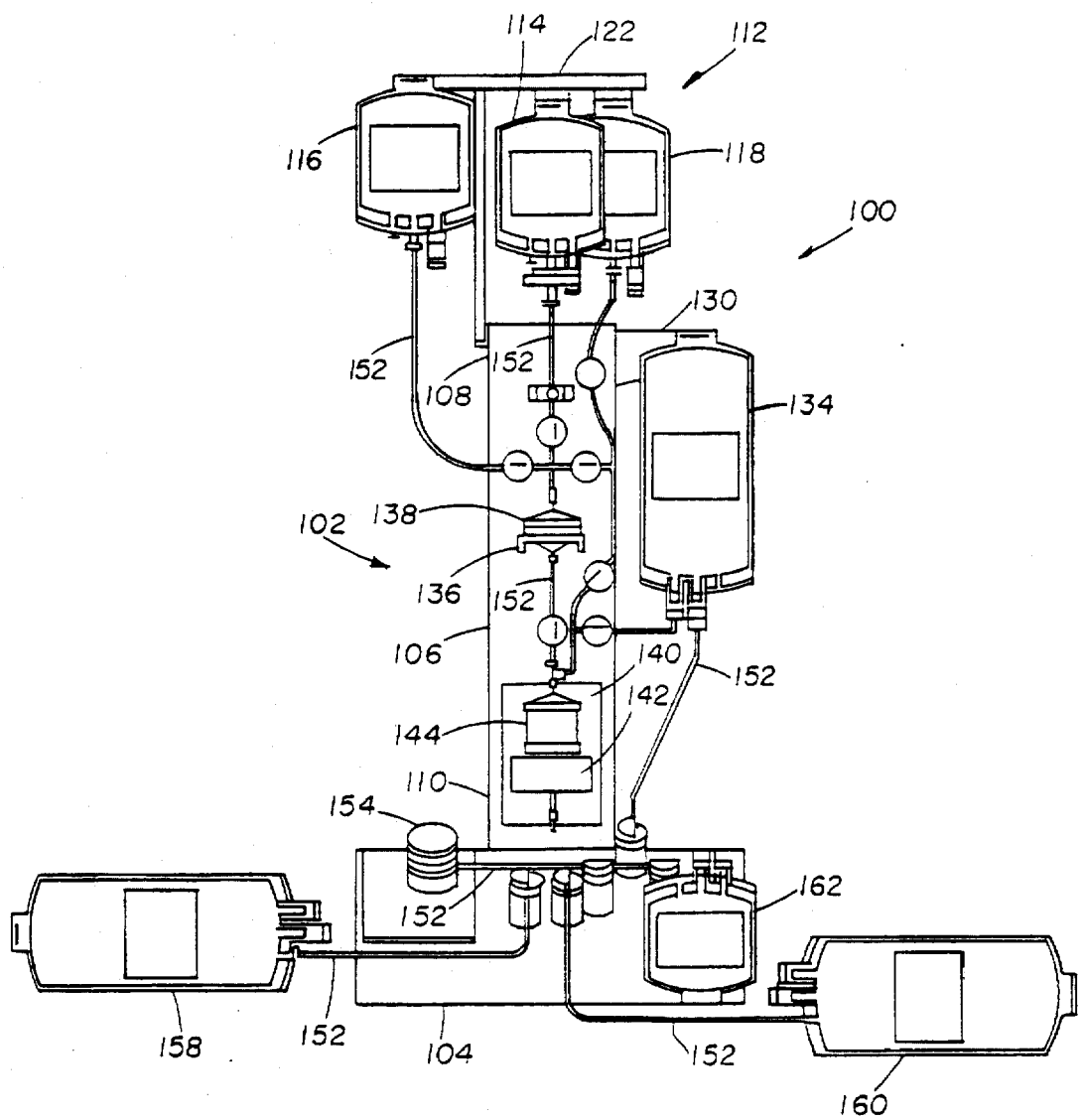
FIG. 1 is an illustrative schematic diagram of a representative cell separator device for separating target particles from a sample fluid.
Figure 2:
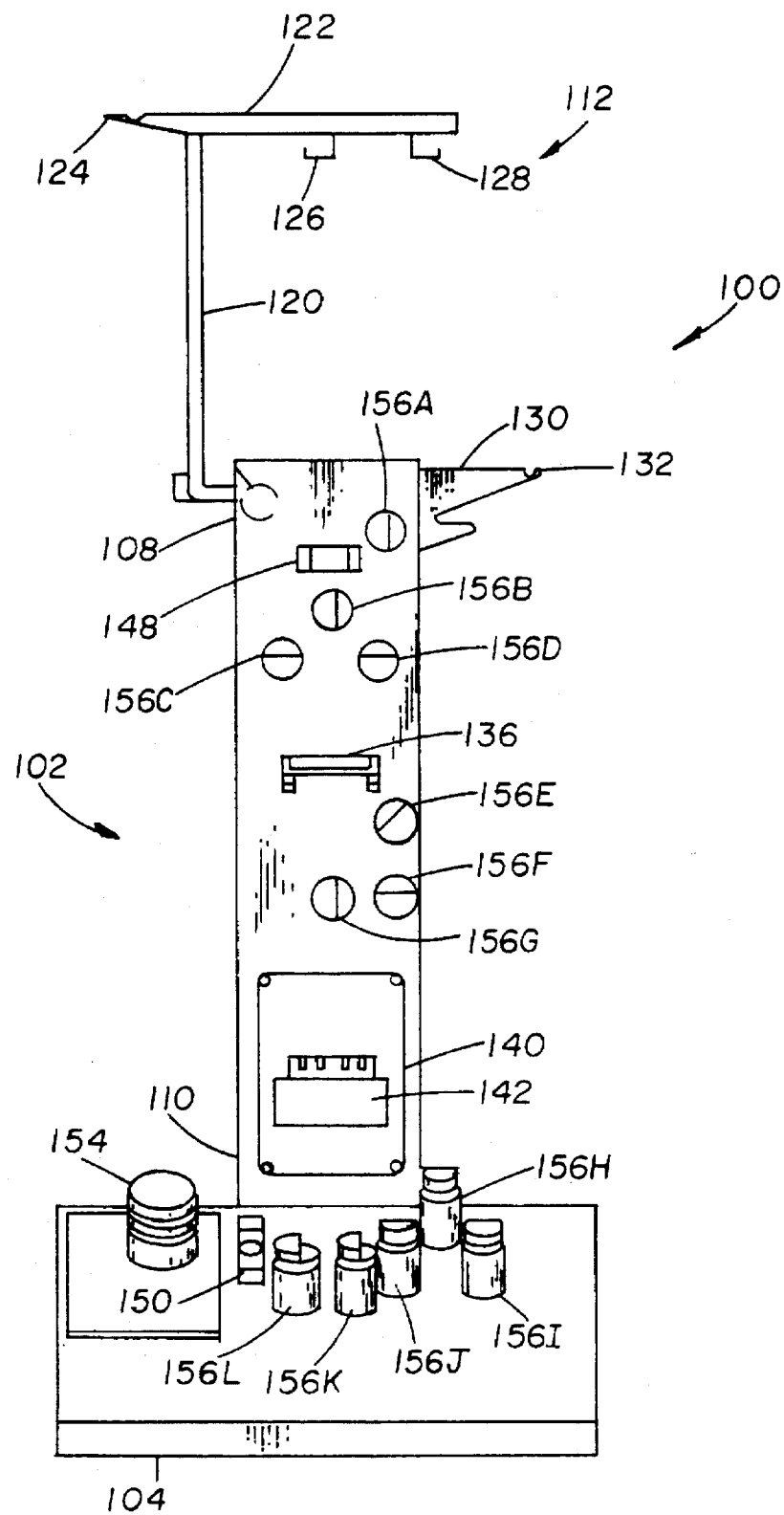
FIG. 2 is an illustrative schematic diagram of the cell separator of FIG. 1 without the removable supply and collection bag and associated tubing.

An improved cell separator 100, illustrated in FIGS. 1 and 2, is provided for separating target cells from unwanted cells. The cell separator 100 includes a frame 102 having a base 104 and a support tower 106. The support tower has a top 108 and bottom 110 wherein the bottom 110 is fixed to the base 104. The base 104 is constructed for resting on a substantially horizontal surface such that the support tower 106 extends upright from the base 104. In this construction, the base 104 provides a substantially stable foundation for supporting the support tower 106.

The cell separator 100 also includes a bag holder 112 for receiving a sample fluid supply bag 114, and first and second fluid supply bags 116 and 118, respectively. The sample fluid supply bag 114 is provided for supplying the sample fluid to the cell separator 100. Similarly, the first and second fluid supply bags 116 and 118 are provided for respectively supplying a wash solution and a protein solution to the cell separator 100, each solution for preparing the cell separator for the fluid separation, as will be discussed in more detail below.

The bag holder 112 includes a support rod 120, best illustrated in FIGS. 2 and 3, that is pivotally mounted to the top 108 of the support tower 106 for movement between an upright position wherein the support rod is substantially aligned with the support tower, to a pivoted position, wherein the support rod is angled with respect to the support tower (FIG. 3). The support rod is constructed for pivotal movement with respect to the support tower to enable the sample fluid supply bag 114 and the first and second fluid supply bags 116 and 118 to be easily mounted to the bag holder 112 by a user. In the pivoted position, the fluid bags 114–118 may be both mounted and spiked by a user at substantially eye level. Thereafter, the bag holder 112 is pivoted to the upright position to both move the fluid bags 114–118 out of the user's way, and to enable the user to manipulate other portions of the cell separator 100 at substantially eye level.

In a presently preferred embodiment of the invention, movement of the bag holder 112 with respect to the frame 102 is accomplished by pivoting the bag holder 112 with respect to the top 108 of the support tower 106, as described above. However, other means could be provided for moving the bag holder 112 with respect to the frame 102. As an example, the support tower 106 may be constructed to pivot about first and second pivot points, thereby enabling the bag holder 112 to be lowered with respect to the base 104. As another example, the bag holder 112 may be slideably mounted upon the support tower 106, thereby enabling the bag holder 112 to be moveable with respect to the frame 102.

The bag holder 112 further includes a support beam 122 (FIGS. 1 and 2) fixed to the support rod 120 and positioned substantially transverse to the support tower 106. The support beam 122 includes a plurality of hooks 124–128 (FIG. 2) for receiving the fluid supply bags 114–118.

A fixed bag holder 130 is fixedly mounted to the top 108 of the support tower 106. The fixed bag holder 130 includes a protruding hook 132 (FIG. 2) for receiving a wash fluid source bag 134. The wash fluid source bag 134 is provided for supplying wash solution to the cell separator for cleansing the cell separator during a separation process, as will be discussed in more detail below.

A pre-column holder 136 is fixed to the support tower 106 intermediate the top 108 and bottom 110 thereof. The pro-column holder 136 is provided for receiving a pre-column 138 (FIG. 1). The pre-column 138 is provided for pre-filtering the sample fluid prior to the fluid separation to remove large particles and debris from the sample fluid. The pre-column may comprise any of a variety of commercially available devices for pre-filtering the sample fluid. It will be apparent to those skilled in the art, however, that although the present invention is being described as including a pre-column 138, the pre-column 138 and pre-column holder 136 may be omitted from the cell separator 100 without departing from the invention.

A particularly novel aspect of the subject invention comprises a stirplate assembly 140 that is fixed to the support tower 106 intermediate the pre-column holder 136 and the bottom 110. The stirplate assembly 140 includes a column holder 142 for receiving a column 144. Generally, the column 144 is provided for separating the target particle from the sample fluid. As will be discussed in more detail below, a presently preferred embodiment of the invention employs a column 144 that includes coated beads for positively selecting target cells from the sample fluid. As the sample fluid passes through the column 144, the target cells are retained within the column 144. Advantageously, the stirplate assembly 140 cooperates with the column 144 to provide controlled agitation to the contents of the column 144. Accordingly, after a sufficient quantity of the target cells have been retained within the column 144, the target cell-ligand bond may be broken by controllably agitating the contents of the column 144. Thereafter, the target cells may be eluted from the column 144 and collected as the product of the separation. The construction and operation of the stirplate assembly 140 and the column 144 will be described in more detail below.

The cell separator 100 further includes a sample sensor 148 and a column sensor 150 (FIG. 2) for sensing changes in optical density of fluid flowing in a tubing 152. The sample sensor is fixed to the top 108 of the support tower 106 for sensing changes in optical density of fluid flowing from the sample fluid supply bag 114. The column sensor 150 is fixed to the base 104 of the frame 102 for sensing changes in optical density of fluid flowing from the column 144. Each of the sample sensor 148 and column sensor 150 comprises an optical sensor 400, illustrated in FIG. 4.

With reference to FIG. 4, the optical sensor 400 includes an optical transmitter 402 mounted in a sensor casing 403 and positioned for transmitting light to an optical receiver 404 (shown in phantom) also mounted in the sensor casing 403. The optical transmitter 402 and receiver 404 are separated by a tube channel 406 constructed for receiving the fluid tubing 152 of the cell separator 100. The optical sensor 400 is constructed for providing a sensor signal indicating the change in optical density of fluid flowing in the portion of the fluid tubing 152 positioned in the robe channel 406.

The optical sensor 400 may be readily constructed by one skilled in the art from commercially available products. In a presently preferred embodiment of the invention, the optical sensor comprises an optical emitter model no. OP133 as available from the Opteck Company, and an optical sensor model no. SP100-11-11-021 as available from the Silicon Detector Company both mounted in a suitable casing. Other constructions for the optical sensor 400 will readily be apparent to those skilled in the art.

Returning to the cell separator of FIGS. 1 and 2, the sample sensor 148 is constructed for providing a sample sensor signal to indicate the change in optical density of the fluid coming out of the sample fluid supply bag 114. The column sensor 150 is constructed for providing a column sensor signal to indicate the change in optical density, of the fluid flowing from the column 144. Both the sample sensor signal and the column sensor signal are provided to a data processor assembly 500 (FIG. 5) for use in controlling the operation of the cell separator 100, as will be described in more detail below.

The cell separator 100 further includes a peristaltic pump 154 for pumping fluid between the plurality of fluid bags 114–118 and 134 and the fluid tubing 152. The peristaltic pump is responsive to a pump control signal provided by the data processor assembly 500 (FIG. 5) for controlling the speed and direction of flow of fluid in the fluid tubing 152. The peristaltic pump 154 is further constructed for providing a pump speed signal to the data processor 500 (FIG. 5). The pump speed signal is indicative of the speed and direction that fluid is being pumped through the fluid tubing. An appropriate peristaltic pump for performing the above-described operation may be readily constructed by one skilled in the art. In a presently preferred embodiment of the invention, the peristaltic pump comprises a Cavro 4708-5 peristaltic pump as provided by Cavro Scientific Instruments, Inc. (Sunnyvale, Calif.). It will be apparent, however, that other apparatus for providing the functions of the peristaltic pump may readily be substituted for the Cavro pump used in a presently preferred embodiment of the invention.

The cell separator 100 includes a plurality of valves 156A–156L (FIG. 2) for controlling the path that the fluid flows through the fluid tubing 152. Each of the valves 156 includes a solenoid (not shown) and plunger 600 (FIG. 6) separated by a valve channel 602 sized to receive the fluid tubing 152. Each valve 156 is responsive to a respective valve control signal for displacing the plunger 600 to collapse the fluid tubing and thereby prevent the flow of fluid through the valve 156. The plurality of valves 156A–156L are positioned to receive respective portions of the fluid tubing 152, thereby to define a plurality of fluid flow paths between the fluid bags. The data processor assembly 500 is constructed to provide the plurality of valve control signals for controlling the path that the fluid flows through the fluid tubing 152, as will be discussed in more detail below.

The cell separator 100 farther includes a data processor assembly 500, illustrated in FIG. 5, that is constructed and programmed for controlling the operation of the cell separator 100. The data processor includes a microprocessor 502 for controlling the operation of the data processor assembly 500. The microprocessor 502 is coupled to a user interface 504 for providing information to and receiving information from a user of the cell separator. The user interface 504 includes a display 506 and a keyboard 508 for respectively providing information to and receiving information from a user of the cell separator. The microprocessor 502 is also coupled to memory 510 that is provided for storing programming instructions and data for controlling the operation of the microprocessor 502. The microprocessor 502 is coupled to an interface 512 for interfacing the data processor assembly 500 with the sample sensor 148, the column sensor 150, the peristaltic pump 154, the plurality of valves 156 and the stirplate assembly 140. It will be apparent to those skilled in the art that although the data processor assembly 500 is described herein by reference to microprocessor 502, user interface 504, memory 510, and interface 512, many other devices could be readily substituted therefor without departing from the true scope and spirit of the present invention. In a presently preferred embodiment of the invention, data processor assembly 500 comprises a personal computer as is commercially available.

With reference to FIGS. 7 and 7A, the stirplate assembly 140 includes a housing 700 having mounted therein a rotating table assembly 702 for generating a moving magnetic field. More particularly, with reference to FIG. 7A, the table assembly 702 comprises a substantially flat circular magnet table 704 having mounted thereon first and second magnets 706 and 708. The magnet table 704 is mounted upon a bearing assembly 710 that rotatably supports the magnet table 704. The stirplate further includes an electric motor 712 mounted exterior to the stirplate housing 700. The electric motor 712 includes a drive wheel 714 coupled to the electric motor 712 via a shaft 716. The electric motor 712 is responsive to a drive signal received from the data processor assembly 500 for rotating the shaft 716 and drive wheel 714. In a presently preferred embodiment of the invention, the electric motor 712 comprises a stepper motor responsive to digital signal for incrementally rotating the shaft 716. It will be apparent, however, to those skilled in the art, that other motors may be readily substituted for the electric motor 712.

A drive belt 718 is coupled to the drive wheel 714 and the magnet table 704 for transferring rotational movement from the electric motor 712 to the magnet table 704. An optical encoder assembly 734 is optically coupled to an encoding wheel 736 of the magnet table 704 for providing a table speed signal indicative of the speed of rotation of the magnet table 704. The table speed signal is provided to the data processor assembly 500 to provide feedback for providing the drive signal, as will be discussed below.

By reference to FIG. 7A, those skilled in the art will appreciate that rotation of the magnet table 704 results in rotation of the magnets 706 and 708 thereby creating a moving magnetic field. It will be apparent, however, that although the stirplate assembly 140 is described herein as generating a moving magnetic field by rotating the first and second magnets 706 and 708, other apparatus, e.g., electromagnetic field generating apparatus, may be provided for generating a moving magnetic field. Further, as will become apparent below, it may be desirable in some applications to create the moving magnetic field by providing other motion to the field generating magnets, e.g., linear motion.

The stirplate assembly 140 also includes a positioning portion 720 mounted to the exterior of the housing 700 on the top thereof, for fixedly receiving the column 144. The positioning portion is fixed to the housing 700 proximate the magnet table 704 so that the moving magnetic field is magnetically coupled to the column 144. A seat portion 722 is constructed to matably receive the column 144 (FIG. 8) to position the column proximate the magnet table 704 so that the moving magnetic field is magnetically coupled to the column 144, as will be described in more detail below. The positioning portion further includes a gripping portion 724 fixed to the seat portion 722 and constructed to engage the exterior of a column to position the column within the stirplate. The gripping portion 724 includes a plurality of extending finger portions 726 each extending upward from the seat portion 722 and ending in a contact portion 728 positioned for contacting the perimeter of the column 144.

The stirplate assembly further includes a position sensor 730 for sensing when the column is positioned in the positioning portion 720 of the stirplate assembly 140. The position sensor 730 comprises a spring actuated switch 732 positioned for engaging the periphery of the column 144 when the column is positioned within the positioning portion 720. The switch 732 is constructed to move linearly inward when the column 144 is properly positioned, to close an electrical contact and thereby provide a column position signal to the data processor assembly 500. The position sensor 730 further comprises a Hall effect sensor 800 (best illustrated in FIG. 8) that is constructed for sensing changes in the magnetic field to thereby determine the position of the first and second magnets 706 and 708 and for providing a stirbar position signal to the data processor assembly 500, indicative of the sensed change in magnetic field. In a presently preferred embodiment of the invention, the data processor assembly 500 is responsive to the stirbar position signal and the table speed signal for modulating the drive signal provided to the motor 712 to thereby control the variation in the moving magnetic field. However, those skilled in the art will recognize that both signals are not required to adequately control the speed of the magnet table 704 under many circumstances.

Figure 9:
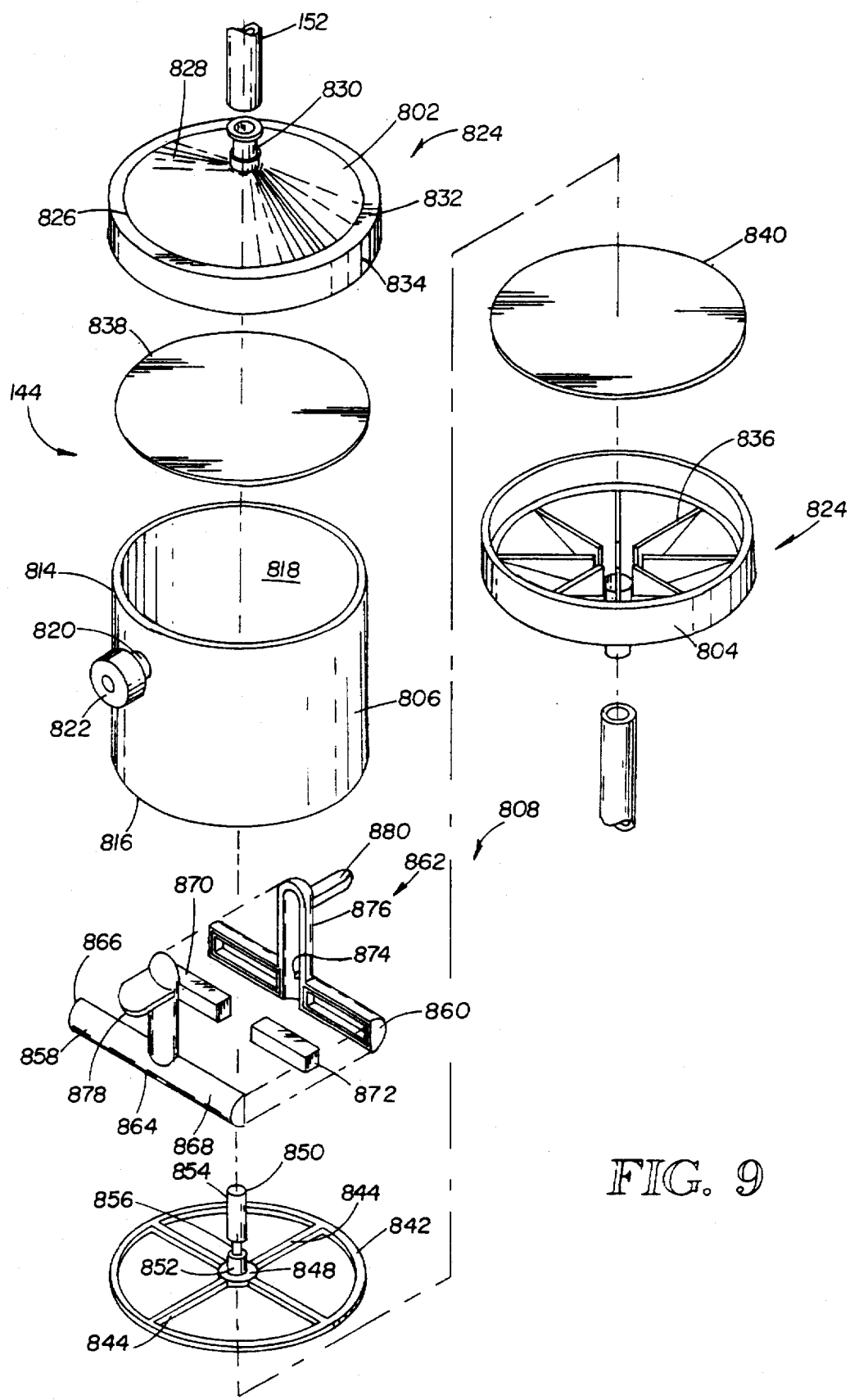
FIG. 9 is an exploded view of the column illustrated in FIG. 8.

With reference to FIGS. 8 and 9, a more detailed description of the construction and operation of the column 144 and stirplate assembly 140 will be provided. As mentioned above, the stirplate assembly includes a seat portion 722 and a gripping portion 724 for fixedly receiving and positioning the column 144. The column 144 includes a top 802 and a bottom 804, each separated by a cylinder 806. Further, the column includes an agitation assembly 808 that is responsive to the moving magnetic field created by the stirplate assembly 140 for agitating the contents of the column 144. In operation, the position sensor 730 determines the variation in magnetic field caused by movement of the stirplate magnets 706 and 708 so that the stirbar position signal is indicative of the speed of movement of the agitation assembly 808. The data processor assembly 500 responds to the stirbar position signal provided by the position sensor 730 to modulate the drive signal provided to the stirplate assembly 140. Accordingly, the data processor 500 is capable of precisely controlling the speed and direction of movement of the agitation assembly and, thereby, precisely controlling the agitation provided to the contents of the column 144.

Further, the tubing 152 that is coupled to the top 802 and bottom 804 of the column 144 includes first and second pressure sensors 810 and 812, respectively. The pressure sensors 810 and 812 each provide pressure signals to the data processor assembly 500. Accordingly, the data processor 500 is capable of determining the pressure differential in the column intermediate the first and second pressure sensors 810 and 812. The data processor assembly 500 responds to the determined pressure in the column 144 to control the overall operation of the cell separator 100, as will be discussed in more detail below.

With reference to FIG. 9, a more detailed description of the column 144 will be provided. The cylinder 806 includes a top portion 814, a bottom portion 816, and an inner channel 818 extending from the top portion to the bottom portion. The top and bottom portions 814 and 816 are open so that the channel 818 extends through the cylinder 806. Advantageously, the cylinder 806 includes a lock inlet 820 and a mating lock inlet cap 822 as is known in the art.

The top portion 802 and bottom portion 804 each include a rim 824 fixed to a base 826 of a hollow frustum 828 and a tube stem 830 fixed to the frustum 828 opposite the rim 824. Preferably, the tube stem 830 is of the type for receiving a lock cap for sealing the column prior to the coupling of the tubing 152 to the column 144. The rim 824 has a substantially circular flange 832 fixed to the base 826 and a substantially cylindrical skirt 834 fixed to the flange 832. The tube stem 830 extends outwardly from the frustum 828 and includes an inner channel for conducting liquid into and out of the top 802 and bottom 804. Each of the top and bottom further include a plurality of support ribs 836 extending radially inward from the rim 824 toward the tube stem to provide an inner frustum channel having fluid flow passageways between adjacent ones of the plurality of support ribs 836 so that fluid can flow between the base of the frustum and the inner channel of the tube stem 830. The rims 824 of the top and bottom 802 and 804, respectively, are sealed to the top and bottom portion 814 and 816 of the cylinder with the tube stems 830 extending outward from the cylinder 806.

First and second substantially planar membranes 838 and 840, respectively, each include a substantially circular perimeter to mate with the flanges 832 of the top and bottom. The first and second membranes 838 and 840 are constructed to permit the flow of particles less than a predetermined size and to prevent the flow of particles greater than the predetermined size. In a presently preferred embodiment of the invention, wherein the column 144 is used for cell separation with a coated bead substrate, the membranes 838 and 840 are constructed of a size to prevent the flow of the substrate beads and thereby capture and retain the substrate within the cylinder 806.

A cylinder insert 842 is positioned intermediate the second membrane 840 and the bottom portion 816 of the cylinder. The cylinder insert 842 includes a plurality of base support ribs 844 extending across the diameter of the channel 818 and intersecting substantially at the center thereof to define a base support 848 for a shaft 850. The shaft 850 extends inward of and substantially parallel to the cylinder 806. The shaft includes a base portion 852 fixed to the base support, an extending portion 854 opposite the base portion, and a recessed portion 856 intermediate the base portion and the extending portion. The combination of the cylinder, the first and second membranes, the cylinder insert, and the top and bottom form the column 144 having a fluid flow channel defined from the tube stem 830 of the top 802 through the cylinder 806 to the tube stem 830 of the bottom 804.

The agitation assembly 808 mounted within the channel 818 of the column comprises first and second stirbar portions 858 and 860 that are constructed to be fixed together to define a stirbar 862. The stirbar 862 includes a mounting portion 864 having first and second magnet sections 866 and 868 extending radially outward therefrom. Each of the first and second magnet sections comprises a stirbar magnet 870 and 872, respectively, housed in a substantially cylindrical, nonmagnetic casing. The mounting portion 864 has a through hole of diameter larger than the diameter of the shaft 850. The mounting portion includes first and second projections 874 on opposite sides thereof extending inward of the through hole. The mounting portion is mounted to the recessed portion 856 of the shaft so that the mounting portion rotates freely about the shaft and so that the movement of the mounting portion linearly along the shaft is limited by the engagement of the first and second projections 874 with the recess portion of the shaft 850.

The stirbar 862 further includes a sleeve portion 876 having an interior chamber of diameter greater than the diameter of the extending portion 854 of the shaft 850. The sleeve portion 876 is fixed to the mounting portion 864 so that the extending portion 854 is positioned within the interior chamber and so that the sleeve portion rotates freely about the extending portion. The stirbar 862 further includes first and second propeller blades 878 and 880, respectively. The first and second propeller blades are substantially planar in configuration and are fixed to the sleeve portion 876 so that the lengths of the first and second propeller blades extend radially outward from the sleeve portion and so that the width of the first and second propeller blades is positioned at a diagonal with respect to the axis of rotation of the sleeve portion. The sieve portion is fixed to the mounting portion so that the first and second propeller blades are substantially perpendicular to the first and second magnet sections 866 and 868.

In operation, the first and second stirplate magnets 706 and 708 are magnetically coupled to the stirbar magnets 870 and 872 of the stirbar 862. Accordingly, rotation of the magnets 706 and 708 results in rotation of the stirbar 862. Since the speed of rotation of the magnets 706 and 708 is controlled by the data processor assembly 500, rotation of the stirbar 862 is similarly controlled by the data processor assembly 500. It will be apparent to those skilled in the art that rotation of the first and second stirbar magnets 870 and 872 will impact the change in magnetic field sensed by the Hall effect sensor 800 (FIG. 8). Advantageously, the data processor assembly 500 may be constructed to monitor the stirbar position signal provided by the Hall effect sensor 800 to determine whether the stirbar magnets 870 and 872 are magnetically coupled to the stirplate magnets 706 and 708. Essentially, this monitoring is to determine whether the change in magnetic field is as expected, given the speed of rotation of the magnetic table 704, as determined by the table speed signal.

It will be apparent to those skilled in the art that, although the present invention is described herein by reference to a stirbar 862 having first and second propeller blades 878 and 880 mounted and angled thereto, other apparatus could be provided for responding to the changing magnetic field to agitate the contents of the column 144. However, it has been determined that an extending shaft including an angled propeller blade mounted thereto, as described in a presently preferred embodiment of the invention, provides superior control over the amount of agitation to the contents of the column, than is provided by other stirbar apparatus. Further, it has been determined that the present stirbar apparatus, mounted for rotation within the column, permits control over the agitation superior to that may be attained using stirbars that are permitted free movement within the column.

The cell separator 100 permits substantially hands-free operation by a relatively unskilled operation. Ideally, the fluid bags 114–118 and 134, along with the tubing 152 and column 144, are provided as disposable apparatus constructed for use during only a single separation process.

In operation, the user of the cell separator 100 pivots the bag holder 112 to mount the fluid bags thereon and to spike the fluid bag for operation. The bag holder 112 is then returned to the upright position and the tubing properly placed within the sensors 148 and 150 and the valves 156. Once the cell separator 100 is thus configured for operation, the user need only monitor the operation for abnormal circumstances that cannot be controlled by the data processor assembly 500.

After the user initiates the cell separation process, the data processor assembly 500 selectively opens and closes the valves 156 to permit wash fluid to flow from the wash fluid bag 134 sequentially through the valves 156H, 156J, 156G, 156E, 156C and 156A. This fluid flow acts to remove air from the tubing 152 and column 144 and to cleanse the tubing of impurities that may be in the tubing from its manufacture.

After the initial cleansing, the data processor assembly 500 controls the valves 156 to prime the tubing by allowing fluid to flow from the second fluid supply bag 118 through the valve 156A, the valve 156D, the pre-column 138, the valve 156G, the column 144, the valve 156L and into a waste bag 158. The flow of fluid in this manner primes the column and tubing with a protein solution selected to prevent substantial bonding of the target cells to the tubing.

Subsequently, the microprocessor controls the valves to permit fluid to flow from the first fluid supply bag 116 through the valve 156C, the pre-column 138, the column 144, the valve 156L and into the waste bag 158. Simultaneously, fluid is permitted to flow from the wash fluid source bag 134 through the valve 156F, the column 144, and the valve 156L and into the waste bag 158. This fluid flow permits rinsing of the tubing and column to remove excess protein and to further wash residual material that may be remaining in the tubing and column from manufacture.

After the cell separator 100 has primed the tubing, it runs the cell separation process. Initially, the data processor assembly 500 opens the valves 156C and 156B to wet the tubing and filter, coupling the sample bag 114 to the tubing 152. Thereafter, the valves 156B, 156G, and 156L are controlled with the peristaltic pump to permit slow loading of the sample via the column. During this phase, the sample fluid is slowly permitted to pass through the column so that the target cells may bind with the substrate of the column 144. The unwanted material of the sample fluid is discarded in the waste bag 158. During the loading process, the data processor assembly 500 monitors the sample sensor signal and the column sensor signal to determine whether all of the sample fluid has been provided and to determine whether a significant amount of target cells are being discarded in the waste bag 158. If either of these events occur, the data processor assembly 500 will discontinue the loading step and move to another portion of the cell separation.

During the load sample step of the cell separation, the data processor assembly 500 also monitors the pressure signals provided by the pressure sensors 810 and 812 to determine whether the pressure across the column 144 is above a predetermined maximum pressure. If the pressure increases beyond a maximum, the data processor assembly 500 may reduce the pressure by slowing the pump speed of the peristaltic pump 154. Other alternative steps may be taken in catastrophic cases by the user to further alleviate excess pressure within the column 144. As an example, the user may actually reverse the flow of fluid through the column from a wash bag 160 to the wash fluid source bag 144 to aid in dislodging unwanted materials so that they may be removed from the column to decrease the overall pressure within the column.

As noted above, the data processor assembly 500 monitors the sample sensor signal provided by the sample sensor 148 to determine when the sample fluid supply is empty. Those skilled in the art will appreciate that the optical density of the fluid flowing past the sample sensor 148 will change dramatically at the instant the last portion of the sample fluid passes by the sample sensor 148. At that point, the microprocessor assembly 500 determines that no further sample fluid is available, and that the column should be emptied.

After all of the sample fluid has been passed through the column 144, the microprocessor assembly 500 will wash the column to remove non-specifically bound portions of the sample fluid. The valves 156 will be controlled to permit fluid to flow from the wash fluid source bag 134 to the waste bag 158. During this main column wash step, the microprocessor assembly 500 may be controlled to provide very light agitation to the column by providing a drive signal to the stirplate assembly 140 to slowly rotate the stirbar 862 of the column 144. However, in a presently preferred embodiment of the invention, no agitation is provided during the column wash step.

After the column wash step, the target cells are eluted from the column. During this step, the microprocessor assembly 500 controls the valves 156F, 156J, and 156I to permit fluid to flow from the wash fluid source bag 134 through the column 144 to a stem cell collection bag 162. During this step, the microprocessor controls the agitation provided to the column by the stirplate assembly 140 and the stirbar 862 to optimize the concentration of target cells being collected in the collection bag 162. The microprocessor assembly 500 monitors the column sensor 152 to determine the optical density of the target cells being collected, and thereby maximize concentration of the target cells. The microprocessor assembly 500 may increase the amount of target cells being collected by either increasing the amount of agitation provided to the column or by decreasing the speed at which the peristaltic pump permits target cells to be withdrawn from the column.

It will be apparent to those skilled in the art that although only several presently preferred embodiments of the invention have been described in detail herein, many modifications and variations may be provided without departing from the true scope and spirit of the invention. Accordingly, the invention is not limited except as by the appended claims.

We claim:

1. An apparatus for providing a magnetic field to a column containing substrate beads, comprising:

(a) a column having an inlet, an inner channel and an outlet; and (b) a field generating means for generating a magnetic field within said column such that said substrate beads are mixed.

2. The apparatus of claim 1 wherein said field generating means further comprises:

(a) magnetic table means for supporting and rotating a table magnet, said magnetic table means comprising a substantially circular member having a central aperture;

(b) bearing means for supporting said magnetic table means, said bearing means being constructed to support said magnetic table means in a manner so that said magnetic table means is movable with respect to said bearing means; and (c) motor means for providing the drive force to said magnetic table means, said motor means being responsive to a drive signal for rotating said magnetic table means.

3. The apparatus of claim 1, further comprising a fluid flow channel which passes through said field generating means.

* * * * *